United States Patent [19]

Akimova et al.

[11] Patent Number: 4,479,933

[45] Date of Patent: Oct. 30, 1984

[54] COMPOSITION FOR SEALING WOUND SURFACES

[75] Inventors: Alla Y. Akimova; Valentin M. Buyanov; Eduard I. Galperin; Anatoly B. Davydov; Galina M. Derkach; Vitaly P. Derevyanko; Viktor V. Keshelava; Larisa P. Malyarova; Igor G. Rusakov; Valeria I. Timokhina; Valery I. Chissov, all of Moscow, U.S.S.R.

[73] Assignee: Vsesojuzny Nauchnoissledovatelsky I Ispytatelny Institut Meditsinskoi Tekhniki, U.S.S.R.

[21] Appl. No.: 419,039

[22] Filed: Sep. 16, 1982

Related U.S. Application Data

[63] Continuation of Ser. No. 234,542, Feb. 13, 1981, abandoned.

[30] Foreign Application Priority Data

Feb. 14, 1980 [SU]  U.S.S.R. .............................. 2912942

[51] Int. Cl.$^3$ ............................................. A61K 31/78
[52] U.S. Cl. ................................................... 424/81
[58] Field of Search ......................................... 424/81

[56] References Cited

U.S. PATENT DOCUMENTS

| | | | |
|---|---|---|---|
| 3,559,652 | 2/1971 | Bannitt et al. ....................... | 128/334 |
| 3,608,070 | 9/1971 | Nouvel .................................... | 424/80 |
| 3,699,876 | 10/1972 | Thomsen et al. ................... | 260/41 C |
| 3,759,264 | 9/1973 | Coover et al. ....................... | 128/334 R |
| 4,035,334 | 7/1977 | Davydov et al. ................... | 260/42.21 |
| 4,199,564 | 4/1980 | Silver et al. ........................... | 424/80 |

OTHER PUBLICATIONS

Chemical Abstracts, 83: 207659f, (1975).

Primary Examiner—Leonard Schenkman
Attorney, Agent, or Firm—Steinberg & Raskin

[57] ABSTRACT

A composition for sealing wound surfaces comprises α-cyanacrylic acid ester or a mixture of esters, monoalkyl esters of polyethylene glycol based on primary aliphatic alcohols of the formula; $C_nH_{2n+1}O(C_2H_4O)_mH$, wherein n=10 to 18, m=7–10, and a water-soluble ketone, the components being present in the following proportions, in percent by weight:

| | |
|---|---|
| α-cyanacrylic acid ester or a mixture of esters | 95–75 |
| monoalkyl esters of polyethylene glycol based on primary aliphatic alcohols of the formula: $C_nH_{2n+1}O(C_2H_4O)_mH$, wherein n = 10–18, m = 7–10 | 0.01–0.5 |
| water soluble ketone | 4.5–24.99 |

The composition of the present invention is useful in medical practice for sealing the line of anastomosis sutures, hermetization of wound surfaces of internal organs, for stopping diffuse hemorrage in operations, for endoscopic applications in chronic ulcera, and the like.

4 Claims, No Drawings

COMPOSITION FOR SEALING WOUND SURFACES

This is a continuation of application Ser. No. 234,542, filed Feb. 13, 1981, now abandoned.

The present invention relates to medicine and, more specifically, to a composition for sealing wound surfaces; this composition is useful in medical practice for sealing the line of anastomosis sutures, coating of the wound surfaces of the inner organs, for arresting diffuse hemorrage in operations, endoscopic applications in the case of chronic doudenal or gastric ulcer, etc.

Various compositions employed for coating wound surfaces which are based on esters of α-cyanacrylic acid are known in the art, such as a medical adhesive containing esters of α-cyanacrylic acid having the following general formula:

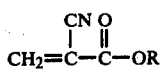

wherein R is a hydrocarbon radical containing 2 to 10 carbon atoms or a composition based on alkoxyalkyl-α-cyanacrylates having the general formula:

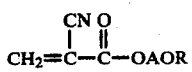

wherein A is a bivalent linear or branched alkylene chain or a hydroxyalkylene radical containing 1 to 8 carbon atoms (U.S. Pat. Nos. 3,759,264; 3,559,652). These compositions form brittle films upon their rapid polymerization in a humid medium. Such films do not ensure hermeticity of the wound surface. Furthermore, alkoxyalkyl-α-cyanacrylates cannot be used in cases where the organism medium has a pH above 7.4, since the rate of biodegradation of polyalkoxyalkyloyanacrylates in alkaline medium is very high and a rapid deterioration of the sealing properties of the film occurs.

Also known in the art is a composition based on ethoxyethyl ester of α-cyanoacrylic acid which has found application as a medicinal adhesive for bonding soft tissues. This composition contains the following components, in percent by weight:

| | |
|---|---|
| 2-ethoxyethyl-α-cyanacrylate | 97–84 |
| polyvinyl-n-butyl ether having units of the formula: | 3–15 |

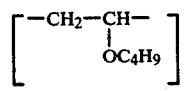

| | |
|---|---|
| and molecular mass of from 4,000 to 10,000 | |
| dyestuff anthraquinone green of the formula: | 0.02–0.1 |

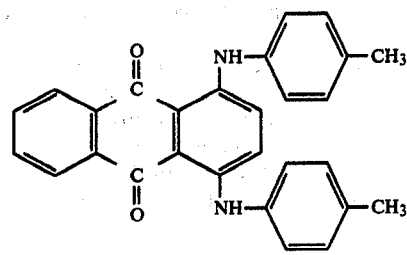

(cf. U.S. Pat. No. 4,035,334; French Pat. No. 7,243,024; British Pat. No. 1,413,132).

Incorporation into this composition of polyvinyl ethers in an amount of from 3 to 15% makes it possible to increase adherence and film elasticity.

However, application of this composition onto the wound surface under the conditions of continuing bleeding and bile oozing does not ensure spreading of the adhesive which results in impaired sealing properties of the forming film. Furthermore, under the conditions of continuing bleeding and bile oozing, very unfavourable conditions are provided for the film-formation from this composition, so that a film is formed which has insufficient sealing properties.

It is the main object of the present invention to improve sealing properties of the composition.

It is another object of the present invention to increase mechanical strength of the resulting film.

Still another object of the present invention is to increase the degree of penetration of the composition into soft tissues.

These and other objects of the present invention are accomplished by the provision of a composition for sealing wound surfaces based on α-cyanacrylic acid esters which, according to the present invention, contains monoalkyl esters of polyethylene glycol based on primary aliphatic alcohols having the formula: $C_nH_{2n+1}O(C_2H_4O)_mH$, wherein $n=10$ to 18, $m=7$ to 10, and a water-soluble ketone, the components being present in the following proportions, in percent by weight:

| | |
|---|---|
| ester of α-cyanacrylic acid or a mixture of esters of α-cyanacrylic acid | 95–75 |
| monoalkyl esters of polyethylene glycol based on primary aliphatic alcohols having the formula: $C_nH_{2n+1}O(C_2H_4O)_mH$, wherein $n = 10$–18, $m = 7$–10 | 0.01–0.5 |
| water-soluble ketone | 4.5–24.99. |

It is preferable to use a composition containing the above-mentioned components in the following proportions, in percent by weight:

| | |
|---|---|
| α-cyanacrylic acid ester or a mixture of esters | 80–90 |
| monoalkyl esters of polyethylene glycol based on primary aliphatic alcohols having the formula: $C_nH_{2n+1}O(C_2H_4O)_mH$, wherein $n = 10$–18, $m = 8$–10 | 0.02–0.3 |
| water-soluble ketone | 9.7–19.98. |

As the esters of α-cyanacrylic acid, it is advisable that the composition according to the present invention contain ethyl-α-cyanacrylate, ethoxyethyl-α-cyanacrylate or butyl-α-cyanacrylate, while as the water-soluble ketone use should be made of dimethylketone or methylethylketone.

The above-mentioned monoalkyl esters of polyethylene glycol based on primary aliphatic alcohols incorporated into the composition according to the present invention comprise products of interaction of ethylene oxide with primary aliphatic alcohols and comprise oily or paste-like substances which are highly soluble in water.

Incorporation of these compounds into the composition according to the present invention ensures a better spreading of the composition over the substrate surface. Furthermore, better conditions of film-formation are provided, which is revealed in increased mechanical strength characteristics. The depth of penetration of the composition into the soft tissues of the organism is increased by 1.5–2 times.

The composition according to the present invention is auto-sterile, and possesses no toxic and irritating effect on the adjacent tissues.

The resulting film is biodegraded under exposure to the organism media. The biodegradation products provide no toxic effect on the organism.

The composition for sealing wound surfaces can be applied directly from a syringe-tube, by spraying, and by means of special apparatus and devices, and can be used for:
  arresting diffuse hemorrage in various operations;
  sealing the lines of anastomosis sutures;
  sealing the wound surface of parenchymatous organs;
  endoscopic applications in the case of chronic duodenal and gastric ulcers; and stopping a pronounced pain syndrome in exacerbation of peptic ulcer, gastric and duodenal hemorrages (bleeding ulcera, decaying stomach tumors, Meylory-Weiss syndrome) with the view to cut them short.

The composition for sealing wound surfaces has been clinically tested on 160 patients.

With the view to stop the diffuse hemorrage in operations on tumors of the retroperitoneal space and small pelvis, the composition according to the present invention has been tested on 15 patients; for reinforcement of sutures of anastomoses—20 patients; for stopping of parenchymatous hemorrage—on 30 patients.

The composition was administered by means of a needle-free injector and a sprayer. The efficiency of hemostasis is good in all cases. No complications associated with the use of the composition according to the present invention in clinics were observed.

The composition for sealing wound surfaces has been used for endoscopic application in patients with chronic duodenal and gastric ulcera, for cutting short a clearly pronounced pain syndrome in the exacerbation of peptic ulcer, for arresting gastro-duodenal hemorrages, as well as for the treatment of defects in the stomach mucous membrane after endoscopic polypectomy—in a total of 95 patients.

The composition according to the present invention is distinguished from known compositions based on α-cyanacrylates by the following advantages: the film resulting from application onto a mucous membrane is more durable and remains intact on the ulcer defect for a substantially longer period. These new qualities of the composition according to the present invention has made it possible to reduce the number of endoscopic applications necessary for ulcer healing.

The composition for sealing wound surfaces according to the present invention is prepared by blending the components dried to a constant weight in a current of a dry inert gas and then packed into sealed polyethylene ampules.

For a better understanding of the present invention the following specific examples illustrating the composition for sealing wound surfaces are given hereinbelow.

EXAMPLE 1

The composition for sealing wound surfaces consists of the following components, g:

| | |
|---|---|
| ethyl-α-cyanacrylate | 30 |
| ethoxyethyl-α-cyanacrylate | 50 |
| monoalkyl esters of polyethylene glycol based on primary aliphatic alcohols of the formula: $C_nH_{2n+1}O(C_2H_4O)_7H$, wherein n = 10–18 | 0.04 |
| methylethylketone | 19.91 |

The components are mixed in an atmosphere of argon and packed into polyethylene syringe-tubes with a capacity of 1 ml. The syringe-tubes are hermetically sealed and placed into glass tubes which are plugged with polyethylene stoppers.

Mechanical strength properties of the thus-prepared composition are determined by the method of pneumopression on rabbits. The composition is applied onto the wound surface directly from a syringe-tube. The tenacity is 70 mm Hg.

The composition has been used in clinics for arresting diffuse hemorrage in operations of tumors of the retroperitoneal space and for sealing the wound surface of parenchymatous organs with positive results.

EXAMPLE 2

The composition for sealing wound surfaces consists of the following components, g:

| | |
|---|---|
| butyl-α-cyanacrylate | 85 |
| monoalkyl esters of polyethylene glycol based on primary aliphatic alcohols of the formula: $C_nH_{2n+1}O(C_2H_4O)_{10}H$, wherein n = 10–18 | 0.03 |
| methylethylketone | 14.97 |

The components are intermixed and the composition is packed as described in foregoing Example 1. The durability properties of the composition as determined by the method of pneumopression are equal to 75 mm Hg.

The depth of penetration into the liver tissue is 1,500μ, the wetting contact angle −16°.

This composition has been used in clinics for sealing wound surfaces of liver, spleen, kidney and has given positive results.

EXAMPLE 3

The composition for sealing wound surfaces consists of the following components, g:

| | |
|---|---|
| ethoxyethyl-α-cyanacrylate | 75 |
| monoalkyl ester of polyethylene glycol based on n-decyl alcohol having the formula: $C_{10}H_{21}O(C_2H_4O)_{10}H$ | 0.5 |
| dimethylketone | 24.5 |

The components are mixed in an atmosphere of argon. The composition is packed as described in Example 1.

The mechanical strength characteristics of the composition determined by the method of pneumopression are 80 mm Hg, the depth of penetration into liver tissue is 2,000μ.

The composition according to the present invention as described in this Example has been used for applications on gastric ulcers, sealing of anastomosis sutures, arresting of diffuse hemorrage with positive results.

EXAMPLE 4

The composition for sealing wound surfaces consists of the following components, g:

| | |
|---|---|
| ethyl-α-cyanacrylate | 20 |
| butyl-α-cyanacrylate | 60 |
| monoalkyl esters of polyethylene glycol based on primary aliphatic alcohols of the formula: $C_nH_{2n+1}O(C_2H_4O)_7H$, wherein n = 10–14 | 0.2 |
| methylethylketone | 19.8. |

The components are mixed in an atmosphere of nitrogen and packed as described in Example 1.

The mechanical strength properties of the composition applied by means of a needle-free injector as determined by the method of pneumopression are equal to 150 mm Hg.

The composition has been used in clinics for application of duodenal and gastric ulcera, for arresting parenchymatous hemorrage and for sealing the wound surface of parenchymatous organs with positive results.

EXAMPLE 5

The composition for sealing wound surfaces consists of the following components, g:

| | |
|---|---|
| ethyl-α-cyanacrylate | 40 |
| ethoxyethyl-α-cyanacrylate | 45 |
| monoalkyl esters of polyethylene glycol based on primary aliphatic alcohols of the formula: $C_nH_{2n+1}O(C_2H_4O)_{10}H$, wherein n = 12–14 | 0.02 |
| dimethylketone | 14.98. |

The composition is prepared by mixing components in a current of nitrogen and then packed as described in Example 1.

The depth of penetration into the liver parenchyma is 2,000μ, the wetting contact angle is −12°.

The mechanical strength of this composition was studied in comparison with the composition consisting of ethyl-α-cyanacrylate and ethoxyethyl-α-cyanacrylate. To this end, on the animals intrapleurally narcotized with hexenal a wide laparotomy was performed and the vascular crus of the organ (liver, spleen, kidney) isolated. The vein was catheterized by means of a thin polyvinylchloride catheter and heparin introduced at the rate of 200 units per one kg of the bodyweight. 30 minutes after the introduction of heparin the planar resection of the organ was performed. A wound surface was thus formed with an area of from 15 to 20 cm². The composition was applied by an injector and the tenacity is determined 15, 30 and 60 minutes thereafter by means of pumping liquid through the catheter. The test results are given in the Table hereinbelow.

The thus-prepared composition was employed in clinics for application of gastric and duodenal ulcera, in exacerbation of peptic ulcer, gastroduodenal hemorrages and has demonstrated positive results.

EXAMPLE 6 (COMPARATIVE)

The composition consisted of the following components, g:

| | |
|---|---|
| ethyl-α-cyanacrylate | 40 |
| ethoxyethyl-α-cyanacrylate | 45. |

The composition was prepared by intermixing of the components and then packed into ampules.

The mechanical strength characteristics of the composition applied by means of a needle-free injector as determined by the method of pneumopression after 15, 30 and 60 minutes are given in the Table hereinbelow.

TABLE

Mechanical-strength characteristics determined by pneumo-pression on rabbits under intensive hemorrage conditions

| | | Mechanical-strength characteristics of the composition, mm Hg | | | | | |
|---|---|---|---|---|---|---|---|
| | | 15 minutes after application | | 30 minutes after application | | 60 minutes after application | |
| | | Composition of Example No. | | | | | |
| No. | Organ | 5 | 6 | 5 | 6 | 5 | 6 |
| 1. | Liver | 95 | 85 | 150 | 95 | 160 | 115 |
| 2. | Kidney | 90 | 61 | 122 | 95 | 140 | 122 |
| 3. | Spleen | 97 | 65 | 127 | 98 | 150 | 120 |

What is claimed is:

1. A composition for sealing wound surfaces consisting of an ester of α-cyanacrylic acid or a mixture of esters of α-cyanacrylic acid, at least one monoalkyl ester of a polyethylene glycol formed by the reaction of ethylene oxide with a primary aliphatic alcohol and having the formula:

$$C_nH_{2n+1}O(C_2H_4O)_mH,$$

wherein n=10 to 18, m=7 to 10, and a water-soluble ketone, the components being present in the following proportions, in percent by weight:

| | |
|---|---|
| ester of α-cyanacrylic acid or mixture of esters of α-cyanacrylic acid | 95–75 |
| monoalkyl ester of polyethylene glycol | 0.01–0.5 |
| water soluble ketone | 4.5–24.99. |

2. A composition according to claim 1, wherein said components are present in the following percentages by weight:

| | |
|---|---|
| ester of α-cyanacrylic acid or mixture of esters of α-cyanacrylic acid | 80–90 |
| monoalkyl ester of polyethylene glycol | 0.02–0.03 |
| water-soluble ketone | 9.7–19.98. |

3. A composition according to claim 1, wherein the ester of α-cyanacrylic acid is ethyl-α-cyanacrylate, ethoxyethyl-α-cyanacrylate, or butyl-α-cyanacrylate.

4. A composition according to claim 1, wherein as the water-soluble ketone dimethylketone or methylethylketone is used.

* * * * *